(12) United States Patent
Majercak et al.

(10) Patent No.: US 7,029,493 B2
(45) Date of Patent: Apr. 18, 2006

(54) STENT WITH ENHANCED CROSSABILITY

(75) Inventors: David C. Majercak, Stewartsville, NJ (US); Hikmat Hojeibane, Princeton, NJ (US)

(73) Assignee: Cordis Corporation, Miami Lakes, FL (US)

( * ) Notice: Subject to any disclaimer, the term of this patent is extended or adjusted under 35 U.S.C. 154(b) by 359 days.

(21) Appl. No.: 10/056,725

(22) Filed: Jan. 25, 2002

(65) Prior Publication Data

US 2003/0144726 A1     Jul. 31, 2003

(51) Int. Cl.
   *A61F 2/06*     (2006.01)
(52) U.S. Cl. .................................... 623/1.15; 606/194
(58) Field of Classification Search ................ 623/1, 623/11, 12, 1.22; 606/191, 192, 194, 195, 606/158, 198, 108; 600/1
See application file for complete search history.

(56) References Cited

U.S. PATENT DOCUMENTS

| | | | |
|---|---|---|---|
| 3,657,744 A | 4/1972 | Ersek | |
| 4,441,216 A | 4/1984 | Ionescu et al. ................ | 3/1.5 |
| 4,503,569 A | 3/1985 | Dotter | |
| 4,512,338 A | 4/1985 | Balko et al. ................ | 128/1 R |
| 4,553,545 A | 11/1985 | Maass et al. | |
| 4,580,568 A | 4/1986 | Gianturco ................... | 128/345 |
| 4,733,665 A | 3/1988 | Palmaz | |
| 4,739,762 A | 4/1988 | Palmaz ....................... | 128/343 |
| 4,760,849 A | 8/1988 | Kropf ......................... | 128/341 |
| 4,776,337 A | 10/1988 | Palmaz | |
| 4,800,882 A | 1/1989 | Gianturco ................... | 128/343 |
| 4,856,516 A | 8/1989 | Hillstead ................... | 128/343 |
| 4,886,062 A | 12/1989 | Wiktor ....................... | 128/343 |
| 4,907,336 A | 3/1990 | Gianturco ................... | 29/515 |
| 4,969,458 A | 11/1990 | Wiktor ........................ | 606/194 |
| 4,990,131 A | 2/1991 | Dardik ......................... | 600/36 |
| 4,990,155 A | 2/1991 | Wilkoff ...................... | 606/191 |
| 4,994,071 A | 2/1991 | MacGregor .................. | 606/194 |
| 5,015,253 A | 5/1991 | MacGregor ................... | 623/1 |
| 5,035,706 A | 7/1991 | Giantureo et al. .......... | 606/198 |
| 5,041,126 A | 8/1991 | Gianturco ................... | 606/195 |
| 5,064,435 A | 11/1991 | Porter ......................... | 623/12 |
| 5,102,417 A | 4/1992 | Palmaz | |
| 5,104,404 A | 4/1992 | Wolff ........................... | 612/1 |
| 5,116,365 A | 5/1992 | Hillstead ....................... | 623/1 |
| 5,122,154 A | 6/1992 | Rhodes ....................... | 606/198 |
| 5,131,908 A | 7/1992 | Dardik et al. ................ | 600/36 |
| 5,133,732 A | 7/1992 | Wiktor ........................ | 606/195 |
| 5,135,536 A | 8/1992 | Hillstead .................... | 606/195 |
| 5,163,958 A | 11/1992 | Pinchuk ....................... | 623/11 |
| 5,171,262 A | 12/1992 | MacGregor ................... | 623/1 |
| 5,176,660 A | 1/1993 | Truckai ...................... | 604/282 |
| 5,178,618 A | 1/1993 | Kandarpa .................... | 606/28 |

(Continued)

FOREIGN PATENT DOCUMENTS

DE        3205942 A1      9/1983

(Continued)

OTHER PUBLICATIONS

*Self-Expanding Endovascular Graft: An Experimental Study in Dogs,* 151 American Journal of Roentgenology, 673-676, Oct. 1988.

*Primary Examiner*—Julian W. Woo
*Assistant Examiner*—Victor Nguyen

(57) ABSTRACT

A stent design is disclosed which has a flexible connector which has flexible arcs and flexible struts aligned similarly to the radial arcs and radial struts, such that the alignment of the flexible connector within the stent decreases the likelihood of the stent's catching on a non-smooth surface.

7 Claims, 3 Drawing Sheets

U.S. PATENT DOCUMENTS

| | | |
|---|---|---|
| 5,192,307 A | 3/1993 | Wall ............................ 623/1 |
| 5,195,984 A | 3/1993 | Schatz |
| 5,217,483 A | 6/1993 | Tower ......................... 606/198 |
| 5,222,971 A | 6/1993 | Willard et al. .............. 606/158 |
| 5,246,445 A | 9/1993 | Yachia et al. ............... 606/108 |
| 5,258,021 A | 11/1993 | Duran ........................... 623/2 |
| 5,266,073 A | 11/1993 | Wall ............................ 623/1 |
| 5,275,622 A | 1/1994 | Lazarus et al. ............... 623/1 |
| 5,282,823 A | 2/1994 | Schwartz et al. ............ 606/198 |
| 5,282,824 A | 2/1994 | Gianturco ................... 606/198 |
| 5,290,305 A | 3/1994 | Inoue |
| 5,292,331 A | 3/1994 | Boneau ...................... 606/198 |
| 5,304,200 A | 4/1994 | Spaulding .................. 606/198 |
| 5,314,444 A | 5/1994 | Gianturco ................... 606/195 |
| 5,314,472 A | 5/1994 | Fontaine ...................... 623/12 |
| 5,334,301 A | 8/1994 | Heinke et al. .............. 204/267 |
| 5,342,387 A | 8/1994 | Summersq .................. 606/198 |
| 5,354,257 A | 10/1994 | Roubin et al. ................. 600/7 |
| 5,354,308 A | 10/1994 | Simon et al. ............... 606/198 |
| 5,366,504 A | 11/1994 | Andersen et al. ............. 623/11 |
| 5,370,683 A | 12/1994 | Fontaine ........................ 623/1 |
| 5,370,691 A | 12/1994 | Samson ........................ 623/12 |
| 5,375,612 A | 12/1994 | Cottenceau et al. ........ 128/899 |
| 5,376,112 A | 12/1994 | Duran ........................... 623/2 |
| 5,382,261 A | 1/1995 | Palmaz ....................... 606/158 |
| 5,387,235 A | 2/1995 | Chuter ........................... 623/1 |
| 5,389,106 A | 2/1995 | Tower ......................... 606/198 |
| 5,395,390 A | 3/1995 | Simon et al. ............... 606/198 |
| 5,397,355 A | 3/1995 | Marin et al. .................. 623/12 |
| 5,403,341 A | 4/1995 | Solar .......................... 606/198 |
| 5,405,377 A | 4/1995 | Cragg ............................ 623/1 |
| 5,411,549 A | 5/1995 | Peters ............................ 623/1 |
| D359,802 S | 6/1995 | Fontaine ................... D24/155 |
| 5,421,955 A | 6/1995 | Lau et al. |
| 5,423,885 A | 6/1995 | Williams ....................... 623/1 |
| 5,441,515 A | 8/1995 | Khosravi et al. ........... 606/194 |
| 5,441,516 A | 8/1995 | Wang et al. ................ 606/198 |
| 5,443,477 A | 8/1995 | Marin et al. ................ 606/198 |
| 5,443,496 A | 8/1995 | Schwartz et al. ............. 623/1 |
| 5,443,498 A | 8/1995 | Fontaine ....................... 623/1 |
| 5,443,500 A | 8/1995 | Sigwart ......................... 623/1 |
| 5,449,372 A | 9/1995 | Schmaltz et al. ........... 606/198 |
| 5,449,373 A | 9/1995 | Pinchasik et al. |
| 5,449,382 A | 9/1995 | Dayton .......................... 623/1 |
| 5,496,365 A | 3/1996 | Sgro |
| 5,527,354 A | 6/1996 | Fontaine et al. |
| 5,569,295 A | 10/1996 | Lam |
| 5,591,197 A | 1/1997 | Orth et al. |
| 5,591,228 A | 1/1997 | Edoga ........................... 623/1 |
| 5,632,763 A | 5/1997 | Glastra ....................... 606/194 |
| 5,643,312 A | 7/1997 | Fischell et al. ............. 606/198 |
| 5,649,952 A | 7/1997 | Lam |
| 5,653,747 A | 8/1997 | Dereume ....................... 623/1 |
| 5,669,924 A | 9/1997 | Shaknovich ................ 606/108 |
| 5,697,971 A | 12/1997 | Fischell et al. |
| 5,700,286 A | 12/1997 | Tartaglia et al. ............... 623/1 |
| 5,720,735 A | 2/1998 | Dorros ........................ 604/284 |
| 5,723,004 A | 3/1998 | Dereume et al. .............. 623/1 |
| 5,728,150 A | 3/1998 | McDonald et al. ............ 623/1 |
| 5,749,825 A | 5/1998 | Fischell et al. ................. 600/3 |
| 5,755,734 A | 5/1998 | Richter et al. .............. 606/194 |
| 5,755,771 A | 5/1998 | Penn et al. ..................... 623/1 |
| 5,782,906 A | 7/1998 | Marshall et al. ............... 623/1 |
| 5,800,508 A | 9/1998 | Goicoechea et al. ........... 623/1 |
| 5,814,061 A | 9/1998 | Osborne et al. ............. 606/194 |
| 5,830,229 A | 11/1998 | Konya et al. ................ 606/198 |
| 5,861,027 A | 1/1999 | Trapp ............................ 623/1 |
| 5,873,906 A * | 2/1999 | Lau et al. .................... 128/898 |
| 5,893,887 A | 4/1999 | Jayaraman .................... 623/1 |
| 5,895,405 A | 4/1999 | Inderbitzen ................. 606/194 |
| 5,906,640 A | 5/1999 | Penn et al. ..................... 623/1 |
| 5,911,754 A * | 6/1999 | Kanesaka et al. .......... 623/1.15 |
| 6,017,363 A | 1/2000 | Hojeibane ...................... 623/1 |
| 6,190,403 B1 * | 2/2001 | Fischell et al. ............ 623/1.16 |
| 6,312,459 B1 * | 11/2001 | Huang et al. .............. 623/1.15 |
| 6,409,761 B1 * | 6/2002 | Jang ........................ 623/6.12 |
| 2003/0167084 A1 | 9/2003 | Orlowski |

FOREIGN PATENT DOCUMENTS

| | | |
|---|---|---|
| EP | 0 540 290 A2 | 10/1992 |
| EP | 0734698 A2 | 3/1996 |
| EP | 0 761 251 A1 | 4/1996 |
| EP | 0800801 A1 | 8/1996 |
| EP | 0830853 A1 | 7/1997 |
| EP | 0 832 616 A1 | 4/1998 |
| EP | 0 937 442 A2 | 8/1999 |
| EP | 0 938 878 A2 | 9/1999 |
| EP | 0 540 290 A3 | 10/1999 |
| FR | 0 566 807 A1 | 4/1992 |
| FR | 2 733 682 A1 | 5/1995 |
| FR | 2 740 346 A1 | 4/1997 |
| GB | 1 205 743 | 9/1970 |
| GB | 0 662 307 A2 | 12/1994 |
| NL | C 1000180 | 12/1996 |
| WO | WO96/26689 | 9/1996 |
| WO | WO 96/29955 A1 | 10/1996 |
| WO | WO 96/34580 | 11/1996 |
| WO | WO 96/34580 A1 | 11/1996 |
| WO | WO 97/15346 A1 | 5/1997 |
| WO | WO97/25000 | 7/1997 |
| WO | WO 97/26840 A1 | 7/1997 |
| WO | WO 97/16217 | 9/1997 |
| WO | WO 98/19628 | 5/1998 |
| WO | WO 98/36709 A1 | 8/1998 |
| WO | WO 98/47447 A1 | 10/1998 |
| WO | WO 99/08744 A1 | 2/1999 |
| WO | WO 01/89414 A1 | 11/2001 |

* cited by examiner

UNEXPANDED    EXPANDED

UNEXPANDED    EXPANDED

STENT WITH ENHANCED CROSSABILITY

FIELD OF THE INVENTION

The present invention generally relates to implantable intraluminal medical devices, particularly stents. The present invention relates to an implantable intraluminal device which is useful for repairing or serving as a conduit for vessels narrowed or occluded by disease or for use in other body passageways requiring reinforcement or the like. More specifically, the present invention discloses an alignment of a flexible connector within a stent which decreases the likelihood of the stent's catching on a non-smooth surface.

BACKGROUND OF THE INVENTION

As background to a discussion of stents, one notes that in the 1970s, the technique of percutaneous transluminal coronary angioplasty (PTCA) was developed for the treatment of atherosclerosis. Atherosclerosis is the build-up of fatty deposits or plaque on the inner walls of a patient's arteries; these lesions decrease the effective size of the artery lumen and limit blood flow through the artery, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guide wire to a point where the sclerotic lesions limit blood flow through the coronary artery. The balloon is then inflated, compressing the lesions radially outward against the wall of the artery and substantially increasing the size of its internal lumen, to improve blood circulation through the artery.

Presently, it is the case that stents are increasingly being used in place of or in addition to PTCA for treatment of atherosclerosis, with the intent of minimizing the need to repeatedly open an atherosclerotic artery. Although a number of different designs for stents have been published, stents are generally configured as elongate cylindrical structures that are provided in a first state and can assume a second, different state, with the second state having a substantially greater diameter than the first state. A stent is implanted in a patient using an appropriate delivery system for the type of stent being implaced within the patient's arterial system. There are two basic types of stents—those that are expanded radially outward due to the force from an inflated angioplasty type balloon, such as the Bx Velocity® and Palmaz-Schatz® stents, made by Cordis Corporation, and those that are self expanding, such as the SMART® stent, made by Cordis Corporation.

Generally, stents, grafts, and graft stents are implantable medical devices (sometimes termed implantable tubular prostheses) which are placed within blood vessels and other body passageways to treat disease conditions such as stenoses, occlusions, and aneurysms. That is, a stent is used as a tubular structure left inside the lumen of a duct to relieve an obstruction. Commonly, stents are inserted into the lumen in a non-expanded form and are then expanded autonomously (or with the aid of a second device in situ. A typical method of expansion occurs through the use of a catheter mounted angioplasty balloon which is inflated within the stenosed vessel or body passageway in order to shear and disrupt the obstructions a associated with the wall components of the vessel and to obtain an enlarged lumen. Transluminal implantation of such devices requires that they be introduced to the site collapsed about or within an introduction device and released to self expand or are expanded by other mechanisms to an expanded tubular state providing a lumen of approximately the same size as the patent vessel or duct lumen.

In the absence of a stent, restenosis may occur as a result of elastic recoil of the stenotic lesion. A number of stent designs have been reported. Such stents include those with rigid ends (8 mm) and a flexible median part of 7–21 mm. This device is formed of multiple parts and is not continuously flexible along the longitudinal axis. Other stent designs with rigid segments and flexible segments have also been described.

Other stents are described as longitudinally flexible but consist of a plurality of cylindrical elements connected by flexible members. These designs have at least one disadvantage if, for example, protruding edges occur when the stent is flexed around a curve, raising the possibility of inadvertent retention of the stent on plaque deposited on arterial walls. This may cause the stent to cause some damage to the interior lining of healthy vessels.

Stents can be viewed as scaffoldings, of generally cylindrical symmetry, that function to physically support, and, if desired, expand the wall of the passageway. Typically, a stent consists of two or more struts or wire support members connected together into a lattice-like or open weave frame. Most stents are compressible for insertion through small cavities, and are delivered to the desired implantation site percutaneously via a catheter or similar transluminal device. Once at the treatment site, the compressed stent is expanded to fit within or expand the lumen of the passageway. Stents are typically either self-expanding or are expanded by inflating a balloon that is positioned inside the compressed stent at the end of the catheter. Intravascular stents are often deployed after coronary angioplasty procedures to reduce complications, such as the collapse of arterial lining, associated with the procedure.

Stents have a lattice-like structure, which leaves spaces defined by the struts that form the stent. Such spaces can allow plaque from the lesion to fall through the stent and enter the blood stream during stent deployment. The spaces can also permit malignant tissue growth through the stent openings into the body passageway and can allow undesired contact between blood flowing through the blood vessel and damaged portions of the vessel. Covered stents, in which a polymeric material surrounds and is attached to the stent, have been proposed to alleviate the problems associated with stent openings.

Diseased vessels are also treated with grafts. Grafts are generally tubular in morphology and are used to replace or create an anatomical passageway to provide a new conduit for fluid, e.g. blood. Grafts are often made from a portion of a vein, but can also be constructed from a synthetic material to form a synthetic graft. Like stents, synthetic grafts can be positioned percutaneously via a catheter, for instance, to be placed at the site of an aneurysm to prevent further dilation and possible rupture of the diseased vessel. In certain instances, the graft material alone does not provide enough structural support for the graft, causing the graft to at least partially collapse and occlude or impede the flow of blood through the vessel. Grafts may be used with stents. For those cases wherein the graft material is synthetic, the combined structure is sometimes referred to as a synthetic stent-graft. Stents are also placed at the ends of synthetic grafts to help secure the ends of the synthetic graft to vessel walls.

The present invention pertains to a manner of arranging the flexible connectors of a stent to reduce the friction between the stent and the wall of the vessel during delivery.

The present invention also reduces the likelihood of protruding edges that occur when the stent is flexed around a curve which increase to a certain degree the possibility of retention of the stent on plaque deposited on arterial walls.

SUMMARY OF THE INVENTION

The present invention is generally directed to the arrangement of the flexible connectors of a stent. The present invention further discloses that the arrangement of flexible connectors can cause the extremal dimensions of openings in the expanded stent to be reduced.

DETAILED DESCRIPTION OF THE INVENTION

Figure 1:
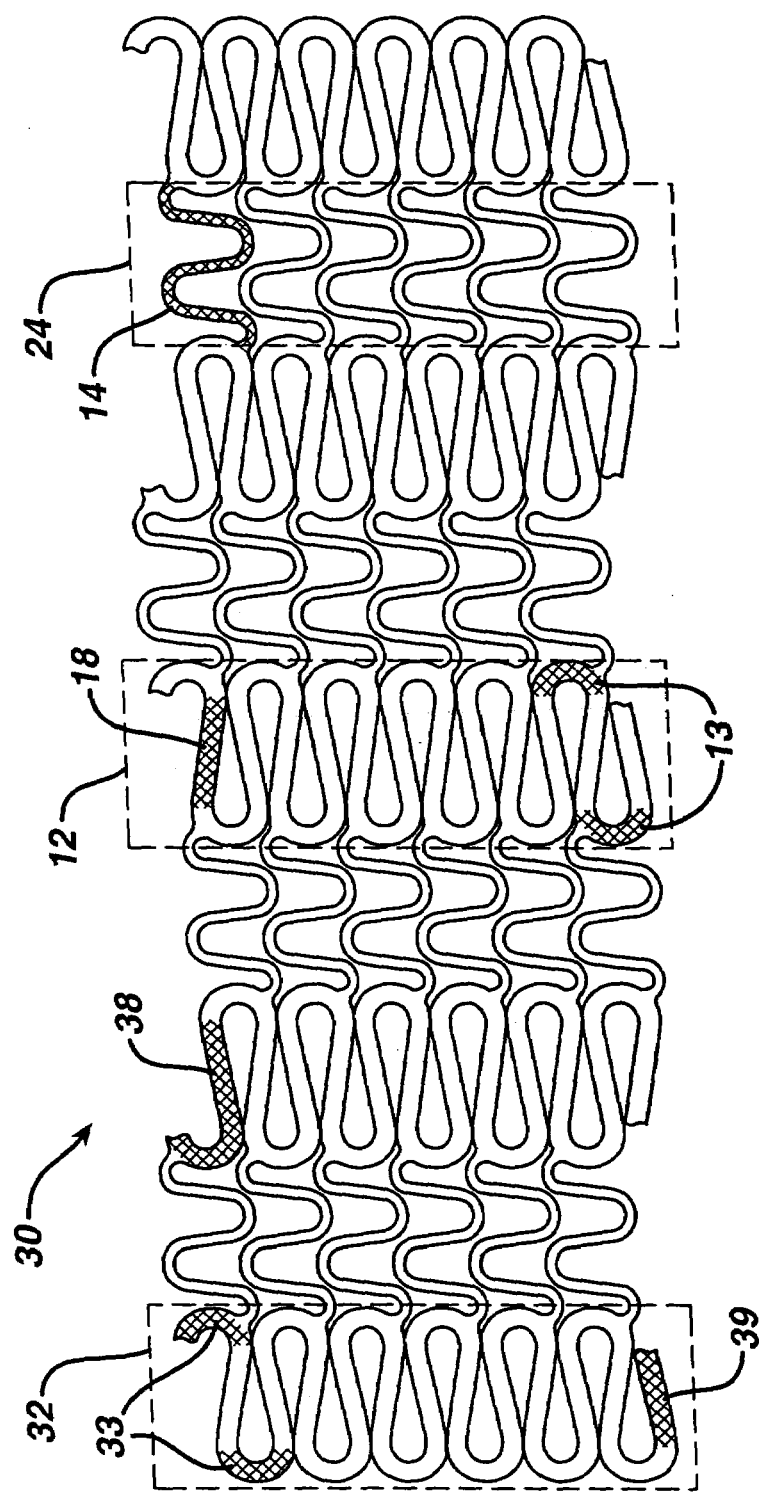
FIG. 1 is a layout view of a prior art stent.

Briefly, FIG. 1 is a flat layout of a prior art stent, described by Fischell et al in U.S. Pat. No. 6,190,403, having a uniform strut width for the circumferential sets of strut members.

Figure 2:
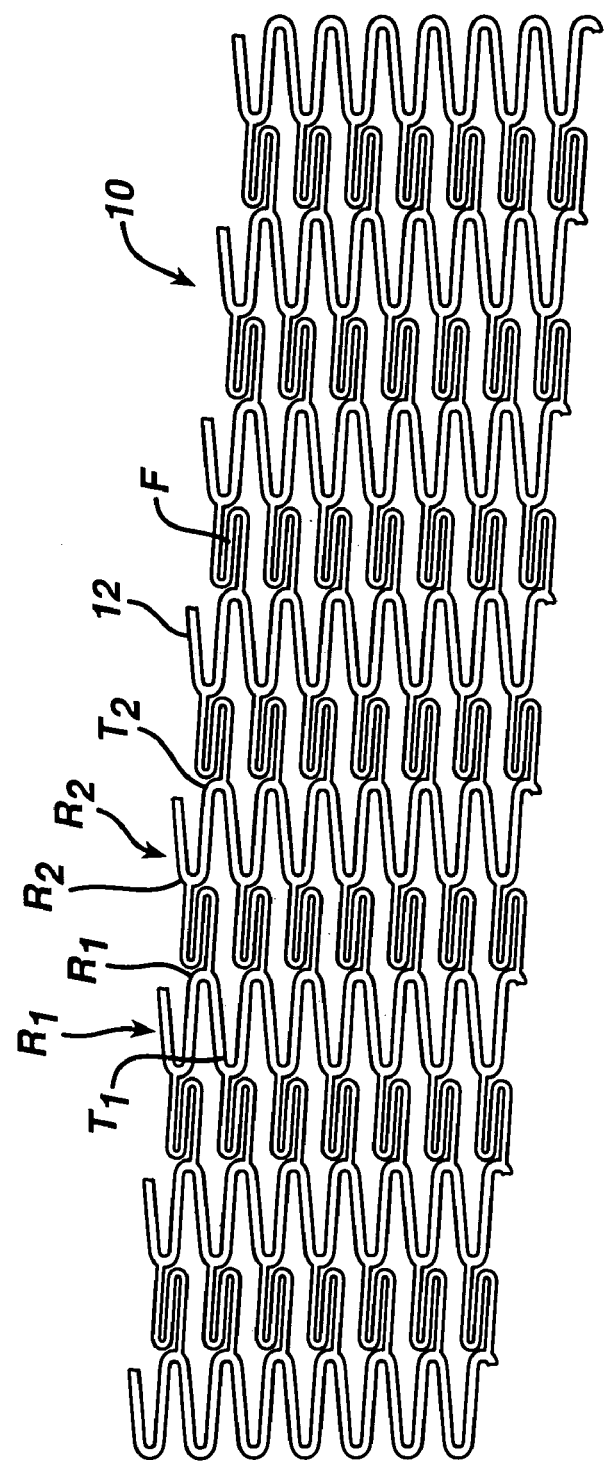
FIG. 2 is a layout view of a stent of the present invention.

FIG. 2. is a flat layout of the stent of the invention, illustrating the radial strut 12 (along the longitudinal axis) and the flexible strut F (along the longitudinal axis). In this embodiment, adjacent rings of radial struts $R_1$, $R_2$ comprise periodic structures which are out-of-phase, meaning that peaks $P_1$ in one ring $R_1$ face peaks $P_2$ in the adjacent ring $R_2$ and that troughs $T_1$ in one Ring $R_1$ face troughs $T_2$ in the adjacent ring $R_2$. In the depicted embodiment, flexible struts link adjacent peaks P of the periodic structure of radial struts R. (In a different embodiment, flexible struts can link non-adjacent peaks.) In other embodiments of the present invention, adjacent rings of radial struts comprise periodic structures which are in-phase, meaning that peaks in one ring face troughs in the adjacent ring, and flexible struts can link peak to trough or peak to peak.

Figure 3:
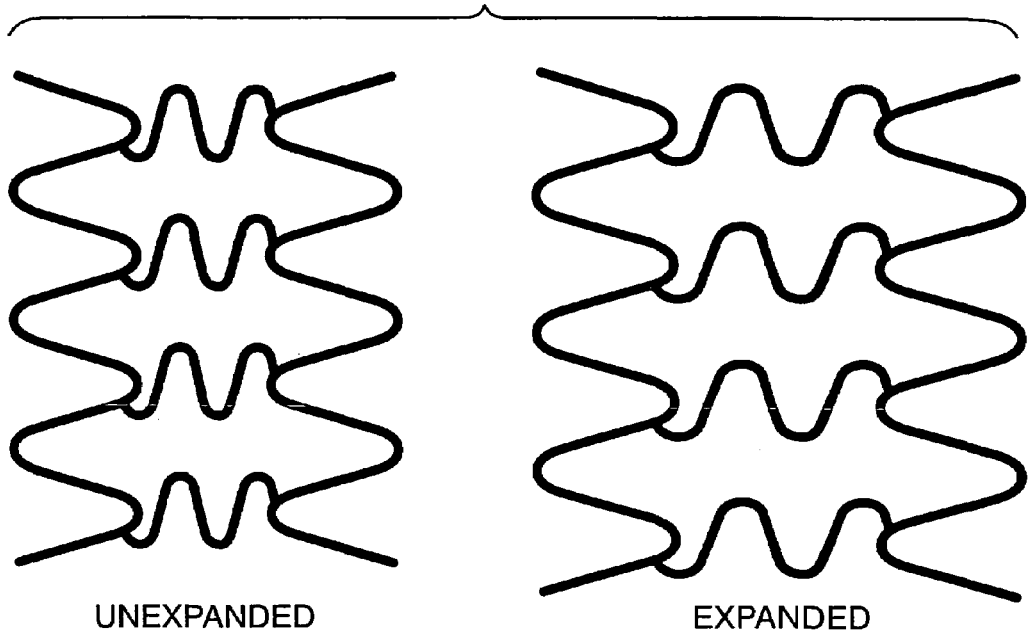
FIG. 3 is a schematic view of an "N" shaped connection in both the expanded and unexpanded stents.

FIG. 3. is a schematic of a stent with an N-connector in the unexpanded and expanded state.

Figure 4:
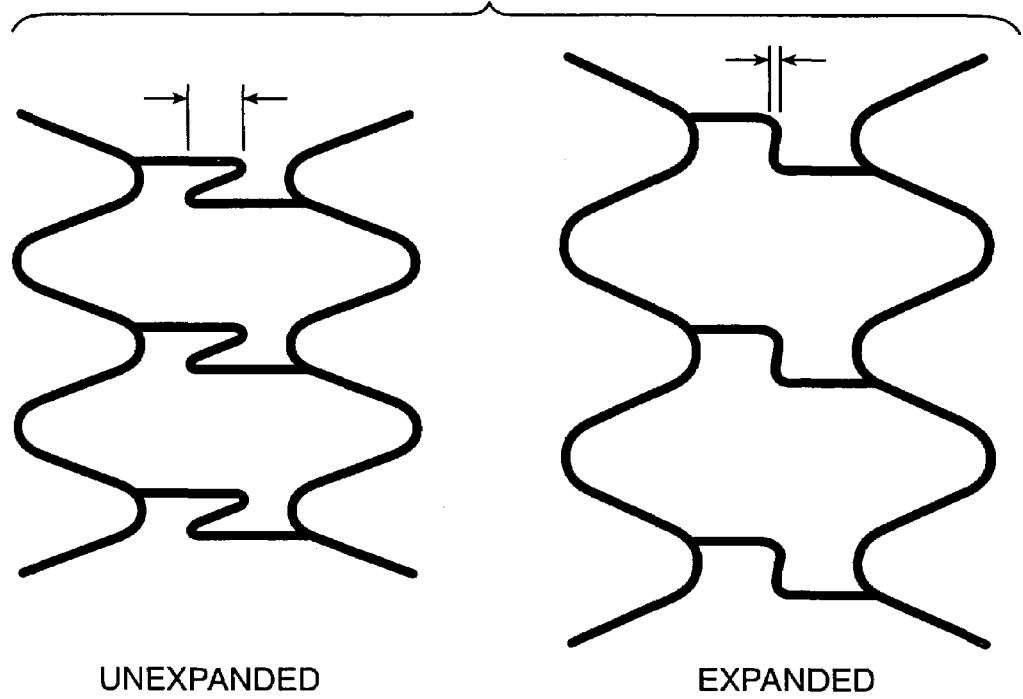
FIG. 4 is a schematic view of a "Z" shaped connection of the present invention in both the expanded and unexpanded stents.

FIG. 4. is a schematic of a stent with a Z-connector in the unexpanded and expanded state, which shows a smaller circular area as the connector rotates into the cell.

Angioplasty, either coronary or general vascular, has advanced to become the most effective means for revascularization of stenosed vessels. Balloon catheter dependent angioplasty has consistently proven to be the most reliable and practical interventional procedure. Other ancillary technologies such as laser based treatment, or directional or rotational arthrectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success including laser based treatment and directional or rotational arthrectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for unstented or otherwise treated vessels; treatments may include adjuvant drug therapy (including drug eluting stents) and other methods mentioned previously.

An example of an early conventional stent is the Palmaz-Schatz® stent made by Cordis Corporation and at least partly described in Schatz, U.S. Pat. No. 5,195,984 (the Schatz Patent). The stent described in the Schatz Patent consists of a series of elongated tubular members having a plurality of slots disposed substantially parallel to the longitudinal axis of the tubular members. The tubular members are connected by at least one flexible connector member.

Some current stent designs such as the CORDIS BX Velocity® stent, Cordis Corporation, Miami Lakes, Fla., have the required flexibility and radial rigidity to provide an excellent clinical result. The present invention may be viewed as a modification over such stents.

Many current tubular stents use a multiplicity of circumferential sets of strut members connected by either straight longitudinal connecting links or undulating longitudinal connecting links. The circumferential sets of strut members are typically formed from a series of diagonal sections connected to curved sections forming a closed-ring, zig-zag structure. This structure opens up as the stent expands to form the element in the stent that provides structural support for the arterial wall. A single strut member can be thought of as a diagonal section connected to a curved section within one of the circumferential sets of strut members. In current stent designs such as the BX Velocity® stent, these sets of strut members are formed from a single piece of metal having a uniform wall thickness and generally uniform strut width. Although a stent with uniform width of the strut members will function, if the width is increased to add strength or radiopacity, the sets of strut members will experience increased strain upon expansion.

FIG. 1 shows a flat layout of an embodiment of a prior art stent described by Fischell et al in U.S. Pat. No. 6,190,403. The stent 5 of FIG. 1 is shown in its crimped, pre-deployed state as it would appear if it were cut longitudinally and then laid out into a flat, 2-dimensional configuration. The stent 5 comprises end sets of strut members 2 located at each end of the stent 5 and three central sets of strut members 6 connected each to the other by sets of longitudinally extending undulating "N" links 4. The end sets of strut members 2 consist of alternating curved sections 7 and diagonal sections 9. The central sets of strut members 6 located longitudinally between the end sets of strut members 2 consist of alternating curved sections 3 and diagonal sections 8.

In the prior art stent 5, the longitudinally diagonal sections 9 of the end sets of strut members 2 are shorter in length than the longitudinally diagonal sections 8 of the central sets of strut members 6. The shorter diagonal sections 9 will reduce the stiff longitudinal length of metal at the ends of the stent 5 to improve deliverability (by reducing "fish-scaling") and will also increase the post-expansion strength of the end sets of strut members 2 as compared with the central sets of strut members 6. In this prior art stent, the width of the curved sections 3 and 7 and the diagonal sections 8 and 9 are all the same. There is no variation in width within any set of strut members or between the end sets of strut members 2 and the central sets of strut members 6. The stent 5 is a design well suited to stainless steel having a wall thickness of 0.0045" or greater, such as found in the CORDIS BX Velocity® stent.

FIG. 3 is a schematic of a stent with a flexible N-connector in both the unexpanded and the expanded state. The longitudinally extending undulating N links define a certain circular area between each pair of N links, shown as a circle "O" and illustrated in the "expanded" state in FIG. 2.

FIG. 4 is a schematic of a stent with a flexible Z-connector in both the unexpanded and the expanded state. The longitudinally extending undulating Z links define a certain circular area illustrated in the "expanded" state in FIG. 3. One can see that there is a smaller circular area as the connector rotates into the cell. A Z link, or something with the symmetry of a "Z", will manifest greater expansion in the circumferential direction than an N-link. This greater extension will lower the distance of closest approach between links about the circumference. The nature of the extension of the Z link, relative to the extension of the N-link, will decrease the distance of closest approach between consecutive Z links along the vertical axis, relative to the distance of closest approach of consecutive N links. The nature of the Z-link, or symmetry related link, relative to the N link, will create a smaller gap between links. The lowered dimension results in enhanced screening or filtering capability.

Thus, an embodiment of the present invention discloses an undulating longitudinal connecting link nominally in the shape of a "Z", as distinct from the prior art which discloses an undulating longitudinal connecting link in the shape of an "N".

Embodiments of the longitudinal connecting link of the present invention encompass undulating connecting links with the following properties. In a two dimensional representation as in FIG. 1, define a Cartesian coordinate system wherein the "x" axis (or horizontal axis) is the longitudinal axis of the figure and the "y" axis (or vertical axis) is the circumferential axis of the figure. An embodiment of the present invention encompasses undulating links wherein each individual link comprises at least two points wherein the tangent is parallel to the y or circumferential axis. In terms analogized to calculus, one would say that each individual link comprises at least two points wherein the first derivative on this graph is infinite.

Embodiments of the longitudinal connecting links comprise an individual undulating link wherein the link has at least two points wherein the tangent is "vertical" and wherein each undulating connecting link possesses a midpoint, such that at the intersection of that midpoint with a circumference of the stent (a vertical line in the two dimensional representation) there is inversion symmetry with respect to that intersection taken as the origin of a Cartesian coordinate system. For each point (x,y) of the undulating connecting member, there is a point (−x, −y).

What is claimed is:

1. A stent in the form of a thin-walled, multi-cellular, tubular structure having a longitudinal axis, the stent comprising:
    a multiplicity of sets of strut members, each set of strut members being longitudinally separated each from the other and each set of strut members forming a closed, ring-like cylindrical section of the stent,
    each set of strut members consisting of a multiplicity of strut elements, each strut element consisting of one curved end strut that is joined at a junction point to one diagonal strut;
    a multiplicity of sets of flexible links with each set of flexible links connecting two of the multiplicity of sets of strut members,
    each set of flexible links consisting of a multiplicity of individual flexible links, each individual flexible link being a single undulating structure that extends generally in the longitudinal direction that is parallel to the stent's longitudinal axis the shape of at least some of the individual flexible links being in the shape of a letter "Z", wherein each of said links has at least two generally curved segments, connected to at least three longitudinal axis of each of the straight segments wherein the longitudinal axis of each of the straight segments of each of the individual flexible links lies generally aligned with the longitudinal axis of the stent.

2. The stent of claim 1 wherein each individual flexible link has two ends, each one of the two ends being fixedly attached to the multiplicity of strut elements thereon.

3. The stent of claim 1 wherein there are adjacent sets of strut members which are in-phase with one another.

4. The stent of claim 1 wherein there are adjacent sets of strut members which are out-of-phase with one another.

5. A stent of approximately cylindrical shape comprising a longitudinal axis and a radial axis, wherein the cross-section approximately perpendicular to the longitudinal axis defines a circumference, the stent comprising:
    a plurality of sets of circumferential members, wherein each set of members forming a closed, ring-like configuration about the circumference and each set of members is longitudinally separated each from the other, wherein each set of members consists of a multiplicity of elements, each element consisting of one curved end;
    a plurality of flexible links, each individual flexible link being a single undulating structure that extends generally along a circumference and each individual flexible link has two ends, each one of the two ends being fixedly attached to the multiplicity of strut elements at an attachment point thereon; and
    wherein the strut elements of the individual flexible links lie aligned with the stent longitudinal axis so that the flexible links when viewed in elevation are formed in the shape of the letter "Z".

6. A stent in the form of a thin-walled, multi-cellular, tubular structure having a longitudinal axis, the stent comprising a multiplicity of circumferential sets of strut members, each set of strut members being longitudinally separated each from the other, each set of strut members being connected to adjacent sets of strut members by longitudinal connecting links, each individual connecting link being a single undulating structure with at least a portion of said connecting links generally extending along a circumference, wherein each single undulating structure is in the shape of a letter "Z" with at least two straight segments aligned with the strut longitudinal axis;
    wherein each of said links has at least two generally curved segments placed generally opposite each other in the longitudinal direction.

7. The stent of claim 6 wherein upon expansion the centers of curvature of the two curved elements undulate around each other so that a link extends parallel to the circumference of the stent.

* * * * *